United States Patent [19]
Rapp et al.

[11] Patent Number: 5,842,469
[45] Date of Patent: Dec. 1, 1998

[54] METHOD FOR EXTENDING THE USEFUL LIFE OF A NASAL DILATOR

[76] Inventors: John D. Rapp, 2801 Alabama St., Bellingham, Wash. 98226; Brian L. Lewis, P.O. Box 1176, Bellingham, Wash. 98227

[21] Appl. No.: 887,517

[22] Filed: Jul. 3, 1997

[51] Int. Cl.[6] .............................. A61F 5/08; A61M 15/00; A61M 16/00; A62B 7/00
[52] U.S. Cl. .............................. 128/200.24; 128/207.18; 606/204.45
[58] Field of Search .............................. 128/200.24, 207.18; 606/199, 204.45

[56] References Cited

U.S. PATENT DOCUMENTS

| | | | |
|---|---|---|---|
| 4,331,138 | 5/1982 | Russell et al. | 128/163 |
| 4,511,608 | 4/1985 | Ferraro | 428/15 |
| 4,653,483 | 3/1987 | Clavin | 128/76.5 |
| 4,745,934 | 5/1988 | Mast et al. | 132/73 |
| 4,824,702 | 4/1989 | Straub | 428/15 |
| 4,890,608 | 1/1990 | Steer | 128/156 |
| 5,284,469 | 2/1994 | Jasen et al. | 602/17 |
| 5,438,777 | 8/1995 | Howell | 40/152.1 |
| 5,476,091 | 12/1995 | Johnson | 128/200.24 |
| 5,533,499 | 7/1996 | Johnson | 128/200.24 |
| 5,533,503 | 7/1996 | Doubek et al. | 128/200.24 |
| 5,546,929 | 8/1996 | Muchin | 128/200.24 |
| 5,549,103 | 8/1996 | Johnson | 128/200.24 |
| 5,553,605 | 9/1996 | Muchin | 128/200.24 |
| 5,611,333 | 3/1997 | Johnson | 128/200.24 |
| 5,611,334 | 3/1997 | Muchin | 128/200.24 |

OTHER PUBLICATIONS

The Chemscope Corp. (Internet Advertisement), 1996, "New Liquid Adhesive Extends The Life of Nasal Dilaters SPTO 10 Times", 3 pages.

Herb Greenberg (Article BusinessInsion), "Can An Entrepenuer Put A Crimp In Breath Right'Style", 2 pages.

Primary Examiner—Kimberly L. Asher
Attorney, Agent, or Firm—Michael R. Schacht; Hughes & Schacht, P.S.

[57] ABSTRACT

A double-sided, pressure-sensitive, adhesive tape which is dimensioned to form a strip for covering a substantial portion of the mounting surface of a previously-used nasal dilator, permitting one side of the strip to be secured to the nasal dilator, and the other side of the strip to be secured to the exterior surface of a human nose, thereby providing a means for reusing and extending the useful life of the nasal dilator which otherwise would be disposed of due to its loss of adhesive bonding capabilities incurred from the prior use.

22 Claims, 5 Drawing Sheets

METHOD FOR EXTENDING THE USEFUL LIFE OF A NASAL DILATOR

FIELD OF INVENTION

The field of the present invention relates generally to the field of nasal dilators, and more specifically to an apparatus and method for extending the useful life of externally-worn nasal dilators which are in the nature of a band mounted to, and extending from the outer wall of one nasal passage, across the bridge of the nose, to the other nasal passage.

BACKGROUND OF INVENTION

A portion of the human population experiences difficulties in breathing through their nose. Several nasal dilator devices have been invented to remedy these difficulties. Nasal dilators are devices which prevent the outer wall tissue of nasal passages from drawing in during breathing. It has been the inventors experience that a particularly effective form of nasal dilator are those which are in the nature of a band attached to the exterior of the nose for extension from one nasal passage, over the bridge of the nose, to the other nasal passage. Examples of these types of nasal dilators are disclosed in U.S. Pat. Nos. 5,476,091 (1995), 5,533,499 (1996), 5,533,503 (1996), and 5,611,333 (1997), all to Johnson; 5,549,103 (1996) to Doubek et al; and 5,546,929 (1996), 5,553,605 (1996), and 5,611,334 (1997) all to Muchin. Each of these patents teach the use of an adhesive coating on the mounting surface of the nasal dilator for releasably securing the nasal dilator to the exterior walls of the nasal passages of a nose. The nasal dilator must remain securely affixed to the exterior of each nasal passage for the nasal dilator to function for its intended purpose of dilating the nasal passages.

A major disadvantage of these known types of nasal dilators is that their adhesive bonding capabilities diminish with use. Eventually the nasal dilator's adhesive mounting surface will fail to securely adhere the nasal dilator to the surface of the nose, and the wearer must discard the otherwise still usable nasal dilator. The diminishing effectiveness of the adhesive bonding capabilities of the nasal dilators is generally due to the interaction of humidity, perspiration, facial oils, cosmetics, dirt, or other contaminants with the adhesive present on the mounting surface of the nasal dilator. Typically, the nasal dilator maintains sufficient adhesive strength to remain securely attached to the nasal passages for only a single use. A single use is defined as the period beginning with the initial application of the nasal dilator and ending with the first removal of that nasal dilator from the nose. A single use period may be a relatively short time period, such as 10 minutes, as in the cases of removal of the nasal dilator precipitated by a bout of itching, cosmetic reasons (avoiding a perceived embarrassing social situation caused by the appearance of the nasal dilator), or inadvertent snagging and dislocating of the nasal dilator on a pillow or other object. In some cases the nasal dilator is not removed until after a longer period, or until it has fulfilled its initial desired use period of the wearer, such as overnight, or for the duration of an athletic event. In all of the mentioned circumstances, regardless of the duration of the single use, the nasal dilator will lose a large degree of its adhesive bonding strength and capabilities. This loss of adhesive bonding strength virtually eliminates the possibility of reusing the same nasal dilator a second time, thereby forcing the user to discard the entire nasal dilator after the single use. The single-use, disposable nature of these nasal dilators unduly increases both the manufacturers and the consumers(wearers) cost by requiring an entire new nasal dilator device to be respectively produced or applied(worn) after each use. Additionally, the disposable nature of these nasal dilators also creates undo waste and excessive filling of landfills.

Currently the only known method for reusing or re-attaching these nasal dilators is with the use of a glue or specialized liquid adhesive, which is marketed under the name Re-Adhese (Trademark) available from DeVore Development Systems. The use of this specially formulated glue requires the user to first apply the glue to the previously-used nasal dilator which has lost the required degree of adhesive strength to remain securely attached to the nose. Next, the user applies an additional amount of the glue to the exterior of their nose where the nasal dilator is to be attached. Finally, a 1–2 minute drying time must elapse, as specified by the manufacturer, before the nasal dilator can be re-attached to the nose. The use of such a glue is problematic. In general, and based on the warning label on the Re-Adhese (Trademark) product, such a glue is dangerous and must be kept out of the reach of children. Likewise, extreme care must be taken to keep the glue out of the eyes, a particularly perilous procedure given the proximity of the nose in relation to the eyes. Additionally the use of glue to re-adhere the nasal dilator is messy, and does not provide a new, clean, and hygienic surface for the nasal dilators second contact with the skin. This is very undesirable as during the initial use of the nasal dilator its mounting surface will be contaminated with perspiration, facial oils, cosmetics, and dirt where it had been in contact with the user's nose. The lack of a new, clean, and hygienic surface can cause the wearer undesirable skin irritation, clogging of the pores, and other similarly related problems. Additionally, the gluing process fails to provide any appreciable reinforcing element or additional support to the previously-used nasal dilator which may be in a less dimensionally stable condition than it was prior to the initial use. This degradation of dimensional stability of the nasal dilator is in part caused by facial oils and perspiration which are absorbed into the nasal dilator during normal usage, and by the distortion of the nasal dilator which occurs when the user removes the nasal dilator from the nose after the first use. In general the use of glue for re-adhering a nasal dilator to a human nose is messy, time-consuming, dangerous, unduly complicated, unhygienic, causes unpleasant odor and fumes, and fails to provide any appreciable reinforcement to the previously-used nasal dilator.

Specifically there is a need for a simple, practical apparatus and method for reusing and re-attaching a previously-used nasal dilator which has lost the necessary adhesive strength required to remain attached to the outside walls of the nasal passages, thereby prolonging the functional life of an otherwise useless nasal dilator. The apparatus and method should provide a new, clean, and hygienic surface for reattachment of the nasal dilator to the exterior of the nose. Moreover, the apparatus should be safe, relatively free from danger, quick, easy to apply, and add an element of reinforcement to an otherwise expired nasal dilator.

Accordingly several objects and advantages of our invention are:

(a) to provide an apparatus and method for reusing a nasal dilator which reduces waste and promotes recycling by extending the life of an otherwise single-use, disposable nasal dilator device;

(b) to provide an apparatus and method for reusing a nasal dilator which is an inexpensive alternative, and more economical method, for consumers to derive the benefits from nasal dilators;

(c) to provide an apparatus and method for reusing a nasal dilator which makes available a new, clean, and hygienic surface for contact with the surface of the nose;

(d) to provide an apparatus and method for reusing a nasal dilator which reinforces the mounting surface of the previously used nasal dilator;

(e) to provide an apparatus and method for reusing a nasal dilator which is simpler, easier, and faster than was previously possible with the prior art;

(f) to provide an apparatus and method for reusing a nasal dilator which is safer, less hazardous, and less dangerous than was previously possible with the prior art;

(g) to provide an apparatus and method for reusing a nasal dilator which achieves a level of comfort commensurate with the wearing of the original nasal dilator device;

(h) to provide an apparatus and method for reusing a nasal dilator which will allow for a single nasal dilator to be reused multiple times without diminishing the effectiveness of the nasal dilator in opening the nasal passages;

Further objects and advantages of our invention will become apparent from a consideration of the drawings and ensuing description.

SUMMARY OF THE INVENTION

Briefly, the present invention comprises in its preferred embodiment an apparatus and method for extending the useful life of a known form of externally applied nasal dilators, wherein the known form of nasal dilators are in the nature of a band adhered to the exterior surface of the nose, and extending from the outer wall of one nasal passage, across the bridge of the nose, to the outer wall of the other nasal passage. More specifically, the apparatus and method comprises a strip of double-sided, pressure-sensitive adhesive material, dimensioned for covering a substantial portion of the mounting surface of a previously-used nasal dilator. This provides a quick and easy means for reinforcing and reusing the nasal dilator which would otherwise be discarded due to its loss of adhesive bonding capability incurred during the prior use. A still greater increase in service life can be obtained by simply continuing to add additional double-sided strips, in potentially successive overlapping layers, permitting the nasal dilator to be further reinforced and allowing the same nasal dilator to be re-attached to the nose multiple times after its initial use. The strip also provides for easy removal of the nasal dilator from the nose after each successive use.

BRIEF DESCRIPTION OF THE DRAWINGS

The invention will be hereinafter more specifically explained with reference to some exemplary embodiments depicted in the accompanying drawings, wherein like items are indicated by the same reference designations.

REFERENCE NUMERALS IN DRAWINGS

Figure 1:
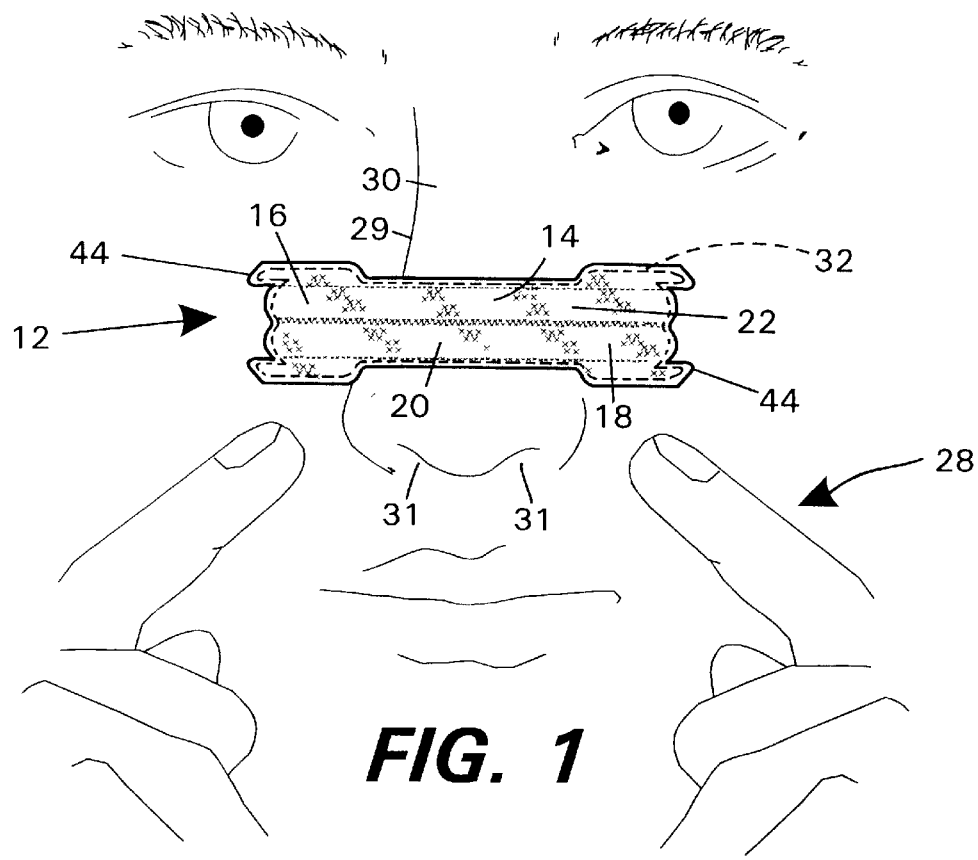
FIG. 1 is a front view of a previously-used nasal dilator which has lost a portion of its original adhesive strength and is in the process of being re-attached to a wearer's nose with a double-sided adhesive strip via one embodiment of the invention.

12 Externally-worn, previously-used, nasal dilator
14 Unitary flexible band
16 First end region
18 Second end region
20 Intermediate segment
22 Resilient member
24 Mounting surface
26 Original adhesive substance
28 Wearer
29 Outer walls
30 Nose
31 Nasal passage
32 Flexible, double-sided, pressure-sensitive, adhesive strip
34 Top release liner
35 Bottom release liner
36 Slit (top release liner)
37 Slit (bottom release liner)
38 Edge (top release liner)
39 Edge (bottom release liner)
40 First adhesive
42 Second adhesive
44 Edge (nasal dilator)
46 Edge (adhesive strip)
48 Double-sided, pressure-sensitive, tape
50 Carrier
55 Unsupported transfer tape
60 Roll
62 Roll
64 Roller
66 Die
67 Waste roll
68 Waste matrix
69 Conveyor
70 First piece
72 Second piece
74 Dispenser

DESCRIPTION

Figure 3:
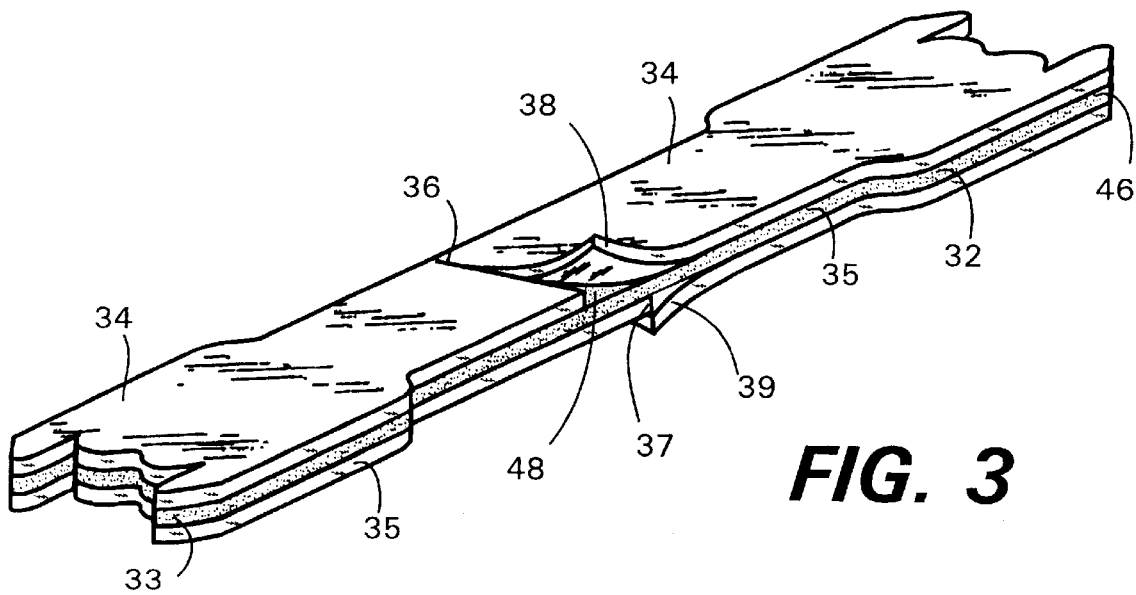
FIG. 3 is a perspective view of the top and bottom release liners being peeled back to expose the top and bottom adhesive surfaces of the double-sided adhesive strip.
Figure 2:
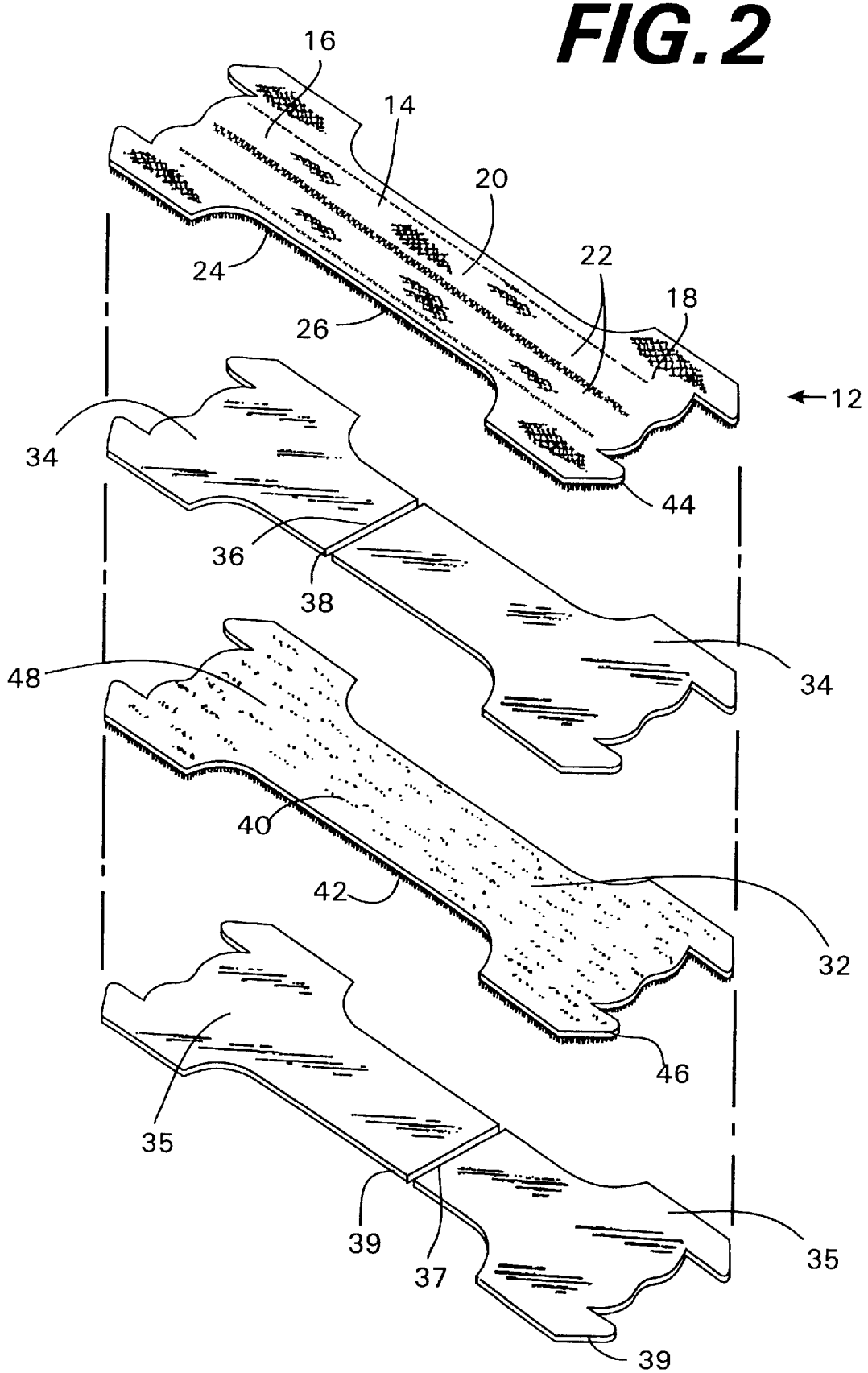
FIG. 2 is an exploded perspective view showing the double-sided adhesive strip, protective top release liner, protective bottom release liner, and a previously-used nasal dilator, in accordance with one embodiment of this invention.

FIG. 1 shows generally a wearer 28 re-attaching an externally-worn, previously-used, nasal dilator 12 to a nose 30 via a flexible, pressure-sensitive, double-sided adhesive strip 32. Adhesive strip 32 is bounded by an edge 46. As best shown in FIGS. 2 and 3, it is preferred that adhesive strip 32 be dimensioned to cover a substantial portion of nasal dilator 12. Furthermore, a first side of adhesive strip 32 is protected by a removable top release liner 34 with an edge 38, and a second side of adhesive strip 32 is protected by a removable bottom release liner 35 with an edge 39. Both top and bottom release liners 34 and 35 are die cut in a manner so that they have essentially the same planar dimensions and shape as strip 32. Furthermore, the top and bottom release liners 34 and 35, each have a slit 36 and 37, to facilitate their removal from strip 32. As best shown in FIG. 2 the previously-used nasal dilator 12 comprises a relatively thin, unitary flexible band 14 having a first end region 16 and a second end region 18 coupled to the first end region by way of an intermediate segment 20. Nasal dilator 12 is bounded by an outer edge 44. Additionally, nasal dilator 12 further includes at least one resilient member 22 which extends longitudinally from first end region 16 to second end region 18. On one side of nasal dilator 12 there is a mounting surface 24 coated with an original adhesive substance 26 which has lost a degree of its adhesive strength due to a previous use.

To extend the useful life of nasal dilator 12 the wearer 28 first bends adhesive strip 32 in an arch-like manner facilitating the separation of edge 38 of top release liner 34 from adhesive strip 32 at slit 36. The wearer would then peel top release liner 34 (see FIG. 2 and FIG. 3) from one side of strip 32 to expose the adhesive on that side and then position and press that side onto mounting surface 24 of nasal dilator 12 in such a manner as to align and mate strip 32 with mounting surface 24. Next, bottom release liner 35 is peeled away in similar fashion, from the other side of strip 32 to expose an adhesive on that side. Next, the mated combination of the nasal dilator 12 and adhesive strip 32 are positioned so that adhesive strip 32 is sandwiched between nose 30, and nasal dilator 12. Finally, pressing in combination, the mated nasal dilator 12 and adhesive strip 32 into the proper position on the surface of the nose 30 (see FIG. 1) such that intermediate segment 20 of nasal dilator 12 is centered at the bridge of the nose 30 and first and second end regions 16 and 18, of nasal dilator 12 are attached to outer walls 29 of nasal passages 31. In this manner strip 32 can be properly positioned and aligned with the mounting surface 24 of the nasal dilator 12, whereas this may not be easily accomplished if the strip 32 was first attached to the nose 30, and subsequently, the nasal dilator 12 was then affixed to the adhesive strip 32. To remove nasal dilator 12 and adhesive strip 32, the wearer simply grasps either an edge 44 of nasal dilator 12 or an edge 46 of adhesive strip 32, and peels the combined assembly of nasal dilator 12 and adhesive strip 32 in a direction away from the surface of the nose 30, thereby breaking the adhesive bond between the strip 32 and the nose 30. If the wearer 28 would like to re-use the same nasal dilator 12 for a third time, she would simply attach a new adhesive strip 32 over the top of the old adhesive strip 32. By applying the adhesive strips in successive, overlapping layers the wearer can achieve multiple uses of a single nasal dilator. In such a manner the adhesive strip 32 of the current invention provides for a new adhesive surface exhibiting the required degree of adhesion necessary for successfully reinforcing, re-attaching, and releasably securing the previously-used nasal dilator 12 to the nose 30.

ADHESIVE STRIP AND LINERS

Figure 5:
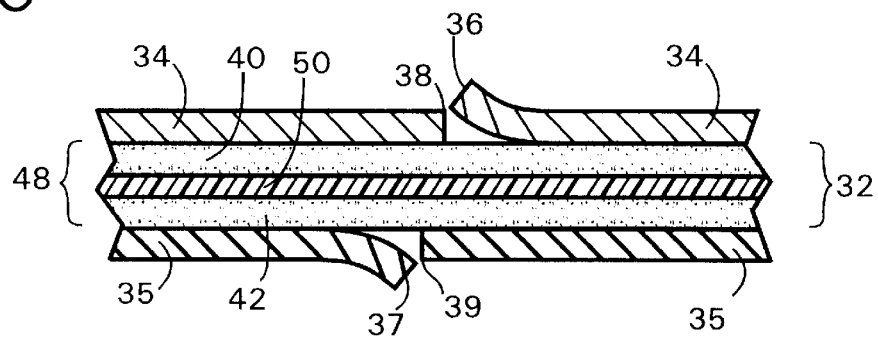
FIG. 5 is a magnified but out of scale view of an edge portion of a double-sided adhesive strip which is constructed of a carrier lining coated with adhesive on each side in accordance with an embodiment of the invention.

In a typical embodiment the adhesive strip 32 and top and bottom release liners 34 and 35, will now be discussed in greater detail. As shown in FIG. 5(side view), strip 32 is constructed from a double-sided, pressure-sensitive tape 48 which comprises a carrier 50, such as a plastic sheet or film, coated on a first side with an adhesive 40 and on a second side with an adhesive 42. Adhesive 40 and 42 are covered respectively by top and bottom release liners 34 and 35.

Specifically, a suitable double-sided adhesive tape available for fabricating adhesive strip 32 is commercially available under the name "Med 6000" manufactured by Avery Dennison, Painesville Ohio. The tape is supplied in roll form with a single protective, semi-bleached, silicone-coated release liner. The tape's construction utilizes a 3 mil clear, polyethylene carrier, coated on both sides with a non-sensitizing, acrylic, pressure-sensitive adhesive. On the unwind side of the roll the non-sensitizing acrylic co-polymer base adhesive is applied to the carrier in a quantity of 63 grams per square meter. The adhesive bonding strength of this side of the tape provides 4.5 lb. force/in width of tape, as measured by the standardized peel force test ASTM D3330-96-B. The adhesive on the other side of the carrier, the side which is in direct contact with the silicone release liner, is applied to the carrier in a quantity of 46 grams per square meter and provides an adhesive strength of 4.0 lb. force/in width as measured under the testing conditions of ASTM D3330-96-B. ASTM test D3330-96-B, titled "Peel Adhesion of Pressure-Sensitive Tape at 180 Degree Angle", is a standardized test offered by The American Society for Testing and Materials (ASTM) for measuring the adhesive properties of double-sided adhesive tape. This test involves pressing a piece of the tape to a clean, flat stainless steel surface. A 3.25 inch diameter, 4.5 lb. roller is used to provide a uniform application force for adhering the tape to the stainless steel surface. Next, an edge of the tape is then peeled at a 180 degree angle from the stainless steel surface at a rate of 12 inches per minute. The test measures the amount of force required to peel the tape under these constants and is expressed in pounds of force per inch width of the tape.

In general, a suitable double-sided tape will exhibit a very high initial tack on the side of the tape which adheres to the skin of the nose. While in many instances the adhesive laminae or layer applied to both faces of the carrier 50 will be of the same composition and have the same adhesive properties, in other instances, the adhesive on the side of the carrier 50 which comes into contact with the skin can be of a different composition than the adhesive which comes into contact with the nasal dilator surface. It has been discovered that even less adhesive bonding strength is required from the side of the adhesive strip 32 which attaches to the mounting surface 24 of the nasal dilator 12 as there is a compounding effect when the adhesive from the strip 32 comes into contact with the original adhesive on the nasal dilator 12. Additionally, when strip 32 is fabricated from a double-sided tape which employs a carrier 50 a desirable degree of reinforcement is added to the nasal dilator 12 providing for a more stable mounting surface 24. An added degree of reinforcement is desirable as this will facilitate the reattachment and proper functioning of nasal dilator 12 which can become flimsy after a single use due to its absorption of facial oil and sweat. Additionally, a double-sided tape suitable for fabricating strip 32 is relatively thin, preferably under 0.0012 in. or 12 mils. This thinness allows for applying multiple strips 32 in successive, overlapping layers, thus allowing wearer 28 to achieve multiple uses of a single nasal dilator 12 without diminishing the dilators effectiveness in urging open the nasal passages.

In another embodiment, also as best illustrated in FIG. 5, strip 32 is manufactured from double-sided adhesive tape 48 which has a breathable carrier 50 and breathable adhesives 40 and 42. Such a tape is available in thickness ranging from 1 to 3 mils from Shurtape Technologies Inc., Hickory N.C. This breathable medical tape has substantially uniform strength in all directions. The carrier 50 is composed of randomly oriented nylon filaments fused at crossover points and is laminated on both sides with a porous layer of pressure-sensitive acrylate adhesive which is permeable to air and moisture and provides good adhesive strength and is hypoallergenic. The breathable nature of this carrier material and adhesive permits moisture to pass through the interstices of the carrier material, reducing moisture buildup on the skin surface beneath the strip 32 thereby inhibiting bacterial growth. Additionally, a breathable carrier material will enable strip 32 to provide a high moisture transmission rate, thereby allowing for increased comfort for the wearer 28 and a prolonged functional adhesive bonding period for strip 32.

Figure 6:
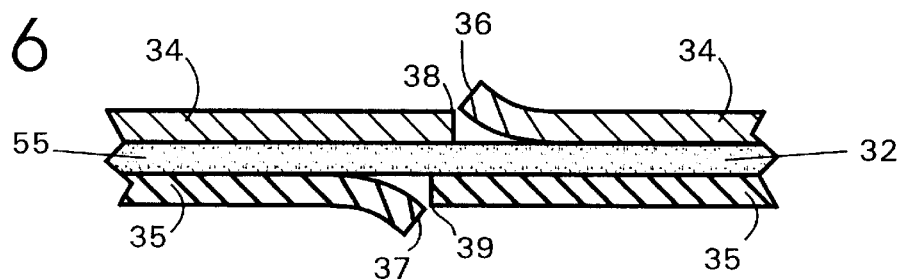
FIG. 6 is a magnified but out of scale view of an edge portion of a double-sided adhesive strip which comprises a transfer film of adhesive which is tacky on both sides, but does not utilize a carrier lining in accordance with an embodiment of the invention.

In another embodiment, as best shown in FIG. 6 (side view), adhesive strip 32 is constructed from a unsupported, double-sided, pressure-sensitive, transfer tape 55 which does not contain a carrier. The transfer tape has an adhesive surface 56 on both planar sides which are protected respectively by release liners 34 and 35. A suitable transfer tape for this embodiment is commercially available under the name "Med 1116" manufactured by Avery Dennison, Painesville Ohio. The tape is supplied in roll form with a single semi-bleached, silicone-coated release liner. This tape is a 1.8 mil clear film of a double-sided, non-sensitizing, acrylic, pressuresensitive adhesive. The extremely thin nature of this transfer tape allows for a greater number of successive layering of the adhesive strips when reusing the same nasal dilator multiple times, than otherwise would be possible with a thicker tape. In general, a transfer tape suitable for fabricating strip 32 is relatively thin, preferably under 0.0012 in. or 12 mils.

Figure 4:
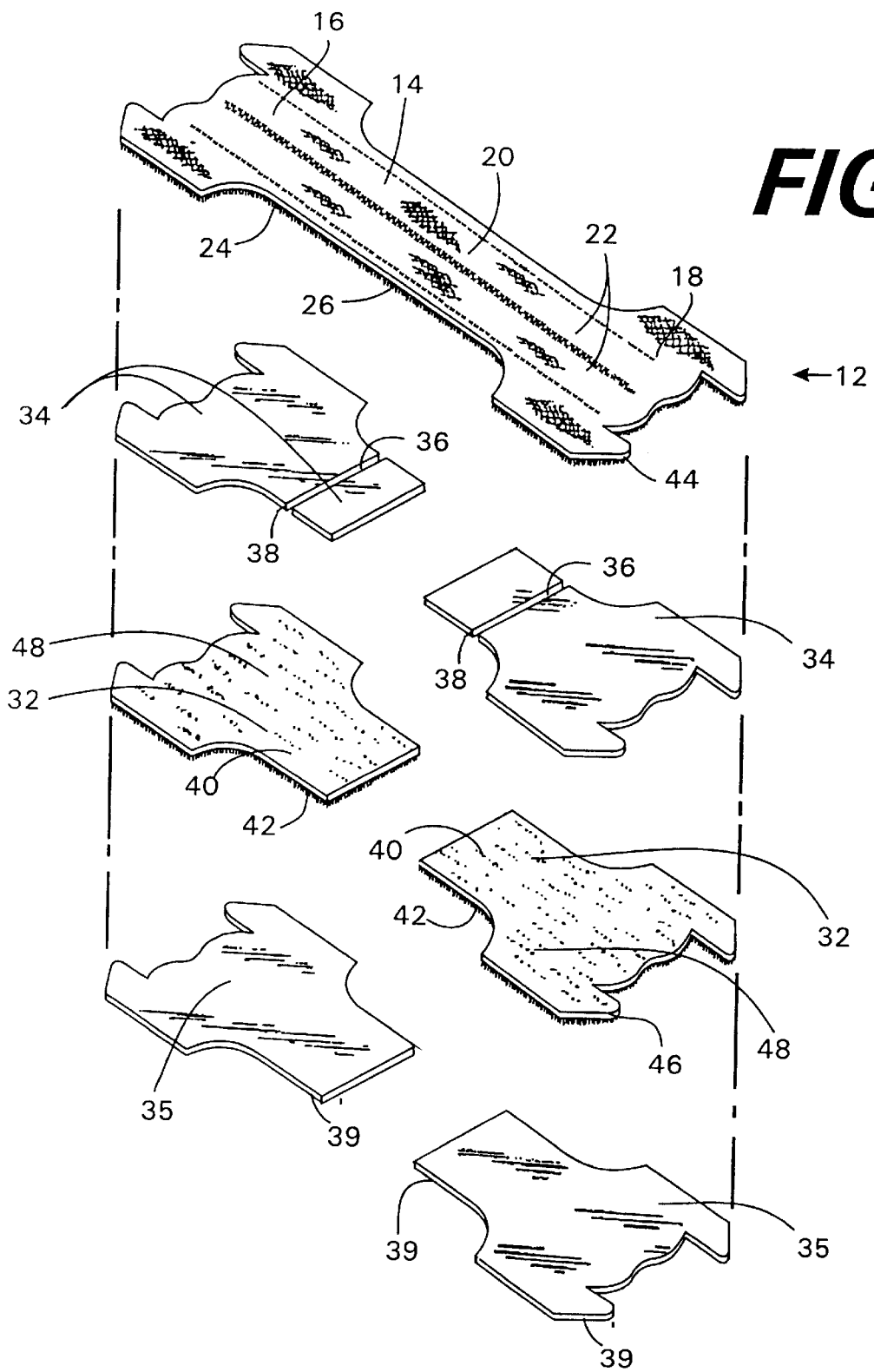
FIG. 4 is an exploded perspective view which shows an embodiment which the adhesive strip comprises a first piece for covering a portion of a first end region and a second piece for covering a second end region of a previously-used nasal dilator in accordance with one embodiment of this invention.

In another embodiment, as best shown in FIG. 4, strip 32 is fabricated into a first piece 70 and a second piece 72. First piece 71 is dimensioned for covering a substantial portion of first end region 16 of nasal dilator 12, and second piece 72 is dimensioned for covering a substantial portion of the second end region 18 of nasal dilator 12. This configuration leaves a portion of intermediate segment 20 of nasal dilator 12 void of a new adhesive surface as otherwise would have been provided if strip 32 was fabricated in a unitary piece. By providing the strip 32 in two separate smaller pieces, wearer 28 may find it easier and more convenient to properly align and mate the first and second pieces 70 and 71, to the mounting surface 24 of the nasal dilator 12.

MANUFACTURING THE STRIP

A method of manufacturing adhesive strip 32 first requires the sandwiching of a double-sided adhesive tape 48 between top and bottom release liners 34 and 35, followed by simultaneously die cutting tape 48 and both release liners 34 and 35, to form strip 32 which is of a shape for substantially covering mounting surface 24 of nasal dilator 12.

Figure 7:
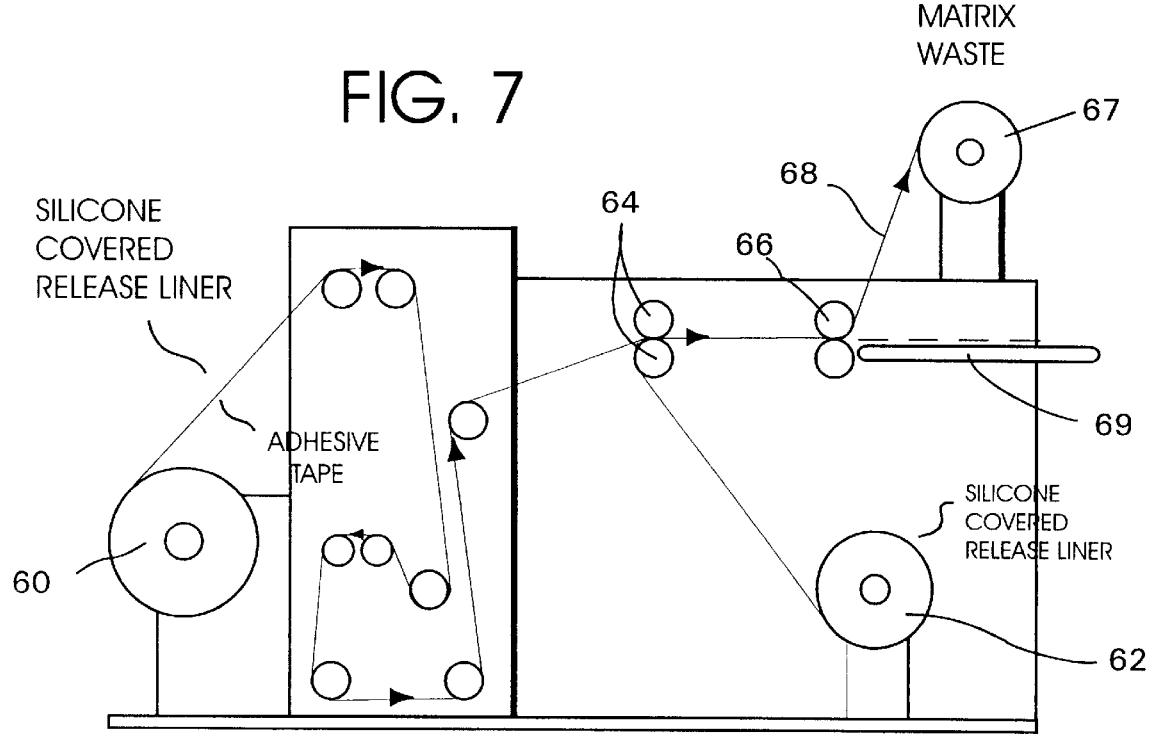
FIG. 7 is a diagrammatic view of a procedure for manufacturing the double-sided adhesive strip in accordance with an embodiment of the invention.

FIG. 7 shows a roll 60 which comprising bottom release liner 35 which has been pre-rolled with double-sided adhesive tape 48. Top release liner 34 is shown separately at a roll 62. In a webbing operation, roll 60, containing bottom release liner 35 and tape 48, are unwound simultaneously with roll 62, containing top release liner 34, and pressed together at a roller 64. Next, the sandwiched tape 48 and protective top and bottom release liners 34 and 35 are cut at a die 66. Die 66 cuts simultaneously through tape 48 and both release liners 34 and 35, producing strip 32 as shown in FIG. 2 and FIG. 3. Die 66 also provides the cuts for slits 36 and 37, whereby the cutting edge of this portion of die 66 only cuts through each respective release liner, leaving tape 48 intact. A waste roll 67 winds up an unwanted waste matrix 68 containing the excess waste portions of the combination of tape 48 sandwiched between top and bottom release liners 34 and 35. The finished die cut individual pieces are transported away via a conveyor 69 for final packaging.

Figure 8:
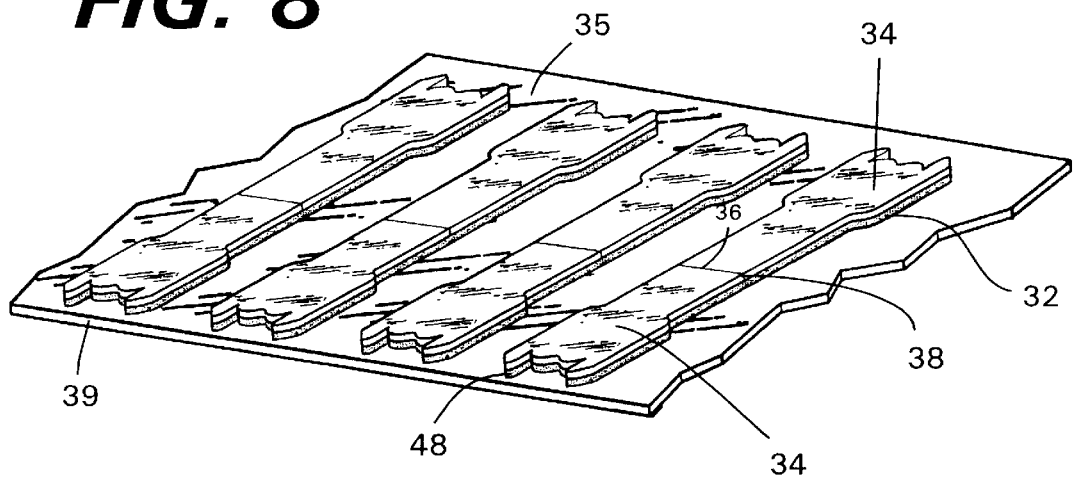
FIG. 8 is perspective view of the adhesive strip manufactured in a nested series in accordance with one embodiment of this invention.
Figure 9:
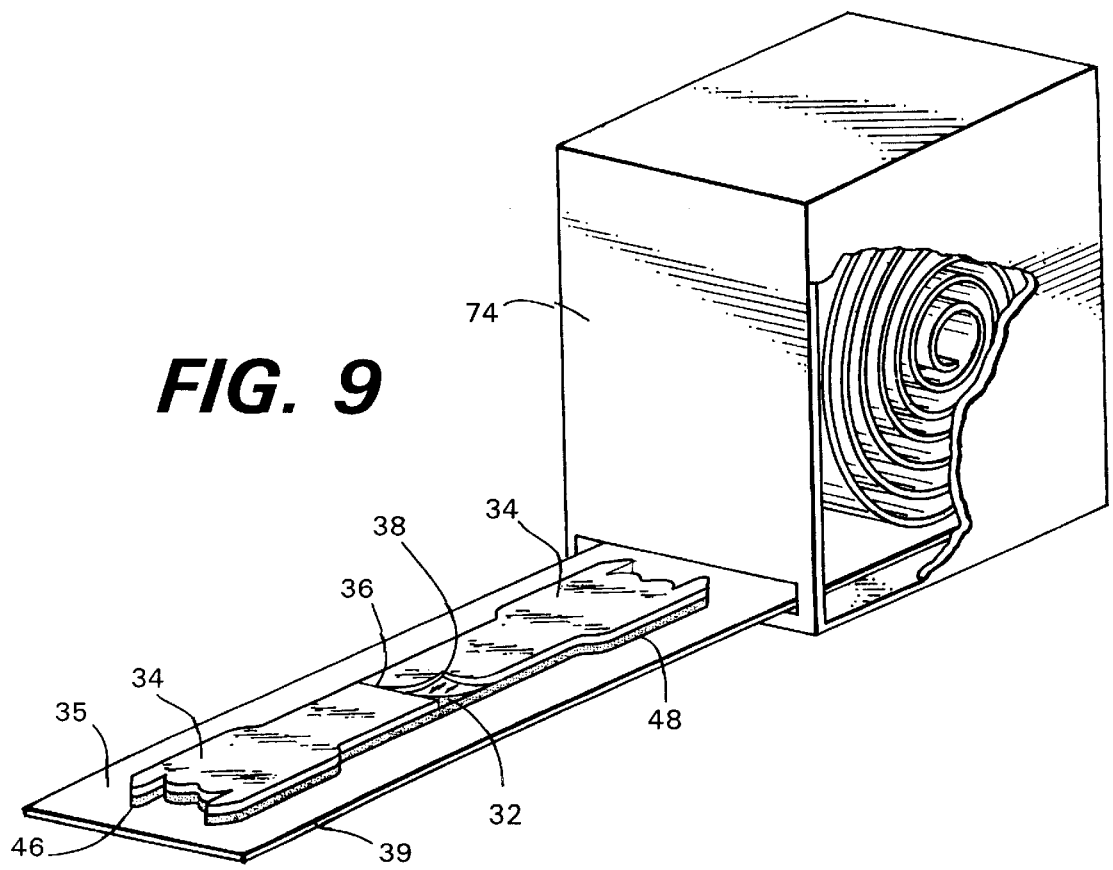
FIG. 9 is a perspective view of a dispenser device which may be utilized to dispense the double-sided adhesive strips with the top release liner shown as slightly lifted to further illustrate the first side of the adhesive strip in accordance with one embodiment of this invention.

In an additional embodiment, best shown in FIG. 8, strip 32 is manufactured in a nested series on a continuous bottom release liner 35. Only minor alterations to the machinery diagrammed in FIG. 7 are required to provide the strip 32 in such a form. The first alteration will require that die 66 be modified to merely perform a kiss cut, whereby die 66 will only cut through top release liner 34 and adhesive tape 48 leaving the bottom release liner 35 intact. In accordance with this embodiment, the waste matrix 68 will only include the unwanted portions of adhesive tape 48 and top release liner 35. The waste matrix 68 is removed and collected via waste roll 67. In such a process multiple adhesive strips are formed in a nested series on the bottom release liner 35 as shown in FIG. 8, which then will be transported away from the machinery via conveyor 69 for future packaging, such as in a dispenser 74 as shown in FIG. 9.

SUMMARY, RAMIFICATIONS, AND SCOPE

The present invention comprises a simple, practical apparatus and method for reusing and reattaching any type of nasal dilator whose function depends upon the dilator being releasably secured to the exterior walls of a human nose, thereby extending the useful life of the nasal dilator, promoting recycling and reducing the consumers cost of procuring an entirely new nasal dilator for each use.

While our above description contains many specificities, these should not be construed as limitations on the scope of the invention, but rather examples of typical embodiments thereof. Many other variations are possible, such as, providing the release liners or adhesive strips in a variety of colors which would facilitate viewing and aligning the adhesive strip with the nasal dilator. Likewise, there are a wide variety of possibilities for altering the means for removing the release liners. Such an alteration could include inserting a tab between the tape and the liner, die cutting the liners in a different or slightly larger shape than the adhesive strip, or by die cutting differently shaped cutout in the release liner rather than slits. Any of these alterations would aid the wearer in the removal of the release liners.

Thus the scope of the invention should be determined not by the embodiments illustrated, but by the appended claims and their legal equivalents.

What we claim is:

1. A method of reusing nasal dilators adapted to be attached to an outer surface of a user's nose to facilitate breathing, the method comprising the steps of:

a nasal dilator comprising an edge having a predetermined dilator edge configuration, a rear surface having first and second adhesive end regions, and a resilient member extending between the first and second end regions, where the first and second adhesive end regions are adapted to be adhered to the outer surface of the user's nose such that the resilient member extends between the first and second end regions to act on the user's nose to facilitate breathing;

using the nasal dilator to obtain a diminished capacity nasal dilator, where the adhesive properties of the first and second adhesive end regions of the rear surface of the diminished capacity nasal dilator are diminished;

providing a strip assembly comprising at least one adhesive strip having front and back adhesive surfaces, at least one front release liner attached to the front adhesive surface, and at least one back release liner attached to the back adhesive surface;

removing the at least one front release liner from the front adhesive surface of the adhesive strip;

forming a repaired dilator assembly by bringing the front adhesive surface of the adhesive strip into contact with the rear surface of the diminished capacity nasal dilator such that the adhesive strip superposes at least one of the first and second adhesive end regions of the rear surface of the nasal dilator and the adhesive strip is adhered to the nasal dilator; and forming a reusable dilator assembly by removing the at least one back release liner from the back adhesive surface of the adhesive strip; wherein the back adhesive surface of the adhesive strip is adapted to be brought into contact with the outer surface of the user's nose such that the first and second end regions of the rear surface of the diminished capacity nasal dilator are arranged on either side of the user's nose, the adhesive strip securely adheres the diminished capacity nasal dilator to the outer surface of the user's nose, and the resilient member extends between the first and second adhesive end regions to act on the nose to facilitate breathing.

2. A method as recited in claim 1, further comprising the steps of:

forming the adhesive strip with a perimeter edge that corresponds to at least a portion of the predetermined dilator edge configuration; and aligning the perimeter edge of the adhesive strip with at least a portion of the edge of the nasal dilator when forming the repaired dilator assembly.

3. A method as recited in claim 1, further comprising the step of forming the adhesive strip such that the adhesive properties of the second adhesive surface are stronger than the adhesive properties of the first adhesive surface.

4. A method as recited in claim 1, in which the step of providing the strip assembly comprises the step of providing a single adhesive strip sized and dimensioned to be superposed over both the first and the second adhesive end regions of the rear surface of the nasal dilator.

5. A method as recited in claim 4, in which the step of providing the strip assembly comprises the step of attaching first and second front release liners to the front adhesive surface and attaching first and second rear release liners to the rear adhesive surface.

6. A method as recited in claim 1, in which the step of providing the strip assembly comprises the step of providing first and second adhesive strips, where the first adhesive strip is sized and dimensioned to be superposed over the first adhesive end region of the rear surface of the nasal dilator and the second adhesive strip is sized and dimensioned to be superposed over the second adhesive end region of the rear surface of the nasal dilator.

7. A method as recited in claim 6, in which the step of providing the strip assembly comprises the step of attaching first and second front release liners to the front adhesive surface of each the first and second adhesive strips and attaching first and second back release liners to the back adhesive surface of each the first and second adhesive strips.

8. A method as recited in claim 1, in which the step of providing a strip assembly comprises the step of providing a plurality of adhesive strip units on a single elongate front release liner, where each adhesive strip unit comprises at least one adhesive strip adapted to be attached to both the first and second adhesive end regions of the rear surface of the nasal dilator.

9. A method of reusing nasal dilators adapted to be attached to an outer surface of a user's nose to facilitate breathing, the method comprising the steps of:

providing a nasal dilator comprising an edge having a predetermined dilator edge configuration, a rear surface having first and second adhesive end regions adapted to adhere to the outer surface of the user's nose, and a resilient member extending between the first and second end regions;

using the nasal dilator to obtain a diminished capacity nasal dilator, where the adhesive properties of the first and second adhesive end regions of the rear surface of the diminished capacity nasal dilator are diminished;

providing a strip assembly comprising an adhesive strip unit comprising at least one adhesive strip having front and back adhesive surfaces, at least one front release liner attached to the front adhesive surface, and at least one back release liner attached to the back adhesive surface, where the adhesive properties of the back adhesive surface are stronger than substantially 4.5 lb. force/in width and the adhesive properties of the front adhesive surface are stronger than substantially 4.0 lb. force/in width;

removing the at least one front release liner from the front adhesive surface of the adhesive strip;

forming a repaired dilator assembly by bringing the front adhesive surface of the adhesive strip into contact with the rear surface of the diminished capacity nasal dilator such that the adhesive strip is adhered to the nasal dilator;

forming a reusable dilator assembly by removing the at least one back release liner from the back adhesive surface of the adhesive strip; wherein the back adhesive surface of the adhesive strip is adapted to be brought into contact with the outer surface of the user's nose such that the first and second end regions of the rear surface of the diminished capacity nasal dilator extend on either side of the user's nose, the adhesive strip securely adheres the diminished capacity nasal dilator to the outer surface of the user's nose, and the resilient member extends between the first and second adhesive end regions to act on the nose to facilitate breathing.

10. A method as recited in claim 9, in which the step of providing a strip assembly comprises the step of providing a plurality of adhesive strip units on a single elongate front release liner.

11. A method as recited in claim 9, in which the step of providing the strip unit comprises the step of providing a single adhesive strip sized and dimensioned to be superposed over both the first and the second adhesive end regions of the rear surface of the nasal dilator.

12. A method as recited in claim 11, in which the step of providing the strip assembly comprises the step of attaching first and second front release liners to the front adhesive surface of the single adhesive strip and attaching first and second rear release liners to the rear adhesive surface of the single adhesive strip.

13. A method as recited in claim 9, in which the step of providing the strip unit comprises the step of providing first and second adhesive strips, where the first adhesive strip is sized and dimensioned to be superposed over the first adhesive end region of the rear surface of the nasal dilator and the second adhesive strip is sized and dimensioned to be superposed over the second adhesive end region of the rear surface of the nasal dilator.

14. A method as recited in claim 13, in which the step of providing the strip assembly comprises the step of attaching first and second front release liners to the front adhesive surface of each the first and second adhesive strips and attaching first and second back release liners to the back adhesive surface of each the first and second adhesive strips.

15. A method as recited in claim 9, in which the adhesive properties of the back adhesive surface are stronger than the adhesive properties of the front adhesive surface.

16. A method as recited in claim 9, in which the adhesive properties of the back adhesive surface are substantially 4.5 lb. force/in width and the adhesive properties of the front adhesive surface are substantially 4.0 lb. force/in width.

17. A method of reusing nasal dilators adapted to be attached to an outer surface of a user's nose to facilitate breathing, the method comprising the steps of:

providing a nasal dilator comprising
an edge having a predetermined dilator edge configuration,
a rear surface having first and second adhesive end regions adapted to adhere to the outer surface of the user's nose,
and a resilient member extending between the first and second end regions;

using the nasal dilator to obtain a diminished capacity nasal dilator, where the adhesive properties of the first and second adhesive end regions of the rear surface of the diminished capacity nasal dilator are diminished;

providing a strip assembly comprising
a strip unit comprising at least one adhesive strip having front and back adhesive surfaces,
at least one front release liner attached to the front adhesive surface,
and at least one back release liner attached to the back adhesive surface, where
the adhesive strip comprises a perimeter edge that corresponds to a portion of the predetermined dilator edge configuration;

removing the at least one front release liner from the front adhesive surface of the adhesive strip;

forming a repaired dilator assembly by
aligning the perimeter edge of the adhesive strip with at least a portion of the edge of the nasal dilator and
bringing the front adhesive surface into contact with the rear surface of the diminished capacity nasal dilator such that the adhesive strip is adhered to the nasal dilator;

forming a reusable dilator assembly by removing the at least one back release liner from the back adhesive surface of the adhesive strip; wherein the back adhesive surface of the adhesive strip is adapted to be brought into contact with the outer surface of the user's nose such that
the first and second end regions of the rear surface of the diminished capacity nasal dilator extend on either side of the user's nose,
the adhesive strip securely adheres the diminished capacity nasal dilator to the outer surface of the user's nose, and
the resilient member extends between the first and second adhesive end regions to act on the nose to facilitate breathing.

18. A method as recited in claim 17, in which the step of providing the strip unit comprises the step of providing a single adhesive strip sized and dimensioned to be superposed over both the first and the second adhesive end regions of the rear surface of the nasal dilator.

19. A method as recited in claim 18, in which the step of providing the strip assembly comprises the step of attaching first and second front release liners to the front adhesive surface of the single adhesive strip and attaching first and second rear release liners to the rear adhesive surface of the single adhesive strip.

20. A method as recited in claim 17, in which the step of providing the strip unit comprises the step of providing first and second adhesive strips, where the first adhesive strip is sized and dimensioned to be superposed over the first adhesive end region of the rear surface of the nasal dilator and the second adhesive strip is sized and dimensioned to be superposed over the second adhesive end region of the rear surface of the nasal dilator.

21. A method as recited in claim 20, in which the step of providing the strip assembly comprises the step of attaching first and second front release liners to the front adhesive surface of each the first and second adhesive strips and attaching first and second back release liners to the back adhesive surface of each the first and second adhesive strips.

22. A method as recited in claim 17, in which the step of providing a strip assembly comprises the step of providing a plurality of adhesive strip units on a single elongate front release liner, where each adhesive strip unit comprises at least one adhesive strip adapted to be attached to both the first and second adhesive end regions of the rear surface of the nasal dilator.

* * * * *